(12) United States Patent
Ueno et al.

(10) Patent No.: US 11,400,315 B2
(45) Date of Patent: Aug. 2, 2022

(54) RADIATION MONITORING DEVICE, RADIATION THERAPY APPARATUS, AND RADIATION MONITORING METHOD

(71) Applicant: HITACHI, LTD., Tokyo (JP)

(72) Inventors: Yuichiro Ueno, Tokyo (JP); Takahiro Tadokoro, Tokyo (JP); Shuichi Hatakeyama, Tokyo (JP); Yasushi Nagumo, Tokyo (JP); Katsunori Ueno, Tokyo (JP); Kouichi Okada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 481 days.

(21) Appl. No.: 16/603,848

(22) PCT Filed: Mar. 6, 2018

(86) PCT No.: PCT/JP2018/008604
§ 371 (c)(1),
(2) Date: Oct. 9, 2019

(87) PCT Pub. No.: WO2019/008825
PCT Pub. Date: Jan. 10, 2019

(65) Prior Publication Data
US 2020/0114172 A1    Apr. 16, 2020

(30) Foreign Application Priority Data
Jul. 7, 2017   (JP) .............................. JP2017-133766

(51) Int. Cl.
*G01T 1/20* (2006.01)
*A61N 5/10* (2006.01)

(52) U.S. Cl.
CPC .......... *A61N 5/1071* (2013.01); *G01T 1/2002* (2013.01); *G01T 1/2006* (2013.01);
(Continued)

(58) Field of Classification Search
CPC .......... A61N 5/1071; A61N 2005/1074; A61N 2005/1076; G01T 1/2002; G01T 1/2006;
(Continued)

(56) References Cited

U.S. PATENT DOCUMENTS

2010/0038547 A1* 2/2010 Ishikawa ................. G01T 1/023
250/369
2013/0341514 A1* 12/2013 Akselrod .................. G01T 1/10
250/363.01
(Continued)

FOREIGN PATENT DOCUMENTS

JP   2001-56381 A   2/2001

OTHER PUBLICATIONS

International Search Report of PCT/JP2018/008604 dated Jun. 5, 2018.

*Primary Examiner* — Marcus H Taningco
(74) *Attorney, Agent, or Firm* — Mattingly & Malur, PC

(57) ABSTRACT

A radiation monitoring device 1 includes a scintillator portion 10 which emits light whose intensity depends on a dose of incident radiation, an optical fiber 20 which transmits photons generated in the scintillator portion 10, a photoelectric converter 30 which converts photons transmitted by the optical fiber 20 to electric signals, a signal counter 40 which counts each of electric signals after being converted by the photoelectric converter 30 with a certain dead time adjusted relative to time width of an irradiation pulse of radiation, a dose calculation unit 50 which calculates a dose from a signal count value counted by the signal counter 40, and a display unit 60 which displays a result of measurement calculated by the dose calculation unit 50.

13 Claims, 7 Drawing Sheets

(52) U.S. Cl.
CPC .............. *A61N 2005/1074* (2013.01); *A61N 2005/1076* (2013.01)

(58) Field of Classification Search
CPC ........... G01T 1/023; G01T 1/161; G21K 5/02; G21K 5/04
See application file for complete search history.

(56) References Cited

U.S. PATENT DOCUMENTS

| | | | |
|---|---|---|---|
| 2014/0252238 A1* | 9/2014 | Jung | G01T 1/2006 250/362 |
| 2017/0059718 A1* | 3/2017 | Masunaga | G01T 1/17 |
| 2018/0246229 A1* | 8/2018 | Preston | G01T 1/16 |
| 2018/0267174 A1* | 9/2018 | Liang | G01T 1/205 |
| 2019/0018148 A1* | 1/2019 | Ueno | G01T 1/29 |
| 2019/0175950 A1* | 6/2019 | Nagumo | G01T 1/2023 |
| 2020/0225366 A1* | 7/2020 | Taguchi | G01T 1/105 |

* cited by examiner

RADIATION MONITORING DEVICE, RADIATION THERAPY APPARATUS, AND RADIATION MONITORING METHOD

TECHNICAL FIELD

The present invention relates to a radiation monitoring device with an optical fiber, a radiation therapy apparatus equipped with such device, and a radiation monitoring method which are advantageously suited for, inter alia, radiotherapy apparatus for treating cancers with radiation.

BACKGROUND ART

A dosemeter described in Patent Literature 1 (Patent Literature 1) comprises "a scintillation fiber which emits light when radiation is incident thereon, an optical transmission fiber to transmit light from the scintillation fiber, a band-pass filter which eliminates noise generated when radiation is incident on the optical transmission fiber and allows light with specific frequencies to pass therethrough, and an optical detection unit which detects light transmitted through the band-pass filter" and with an aim to obtain a local dosimeter capable of taking measurements of high precision, while eliminating noise, particularly, influence of Cherenkov light generated when radiation is incident on the optical transmission unit during measurement of doses inside the body in brachytherapy to perform treatment with small radioactive sources being inserted into the body.

CITATION LIST

Patent Literature

Patent Literature 1: Japanese Patent Application Laid-Open No. 2001-56381

SUMMARY OF INVENTION

Technical Problem

The number one cause of death in Japan is cancers and the number of death from cancer goes on increasing. In Japan of recent years where improvement of medical care quality (Quality of Life: QOL) is required, radiation cancer therapy attracts attention as an approach to cancer treatment. With an enhancement of the degree of precision of radiation cancer therapy technology which is seeds, along with QOL improvement as needs, radiation cancer therapy is becoming poplar widely in Japan as well.

There is a wide variety of radiations for use in therapy, such as X rays, electron beans, proton beams, heavy particle beams, and neutron rays; especially, development of radiotherapy apparatus using proton beams and heavy particles has been outstanding recently.

These proton beams and heavy particle beams have a property in which they give energy intensively immediately before stopping, thus generating a peak of doses (a Bragg peak) and, therefore, such property is utilized to enable concentrating doses on a cancer site; a therapy with low invasiveness and high precision can be expected.

Also, in X-ray therapy, IMRT (Intensity Modulated Radiation Therapy), IGRT (Image Guided Radiation Therapy), etc. are developed and efforts are underway to concentrate doses on a cancer site.

With the progress of radiation therapy apparatus enhancement, improvement of precision in totality concerning radiation therapy is required, including precision of a therapy plan, precision of positioning of a patient, and dose rate measurement for therapy plans and QA (Quality Assurance) of apparatus.

For dose measurement in radiation therapy, an ionization chamber that is good in its stability and reproducibility is widely used. However, the ionization chamber has limitations to downsize it because of its principle of detection and, instead, dose distribution measurement using a semiconductor detector which is comparatively easy to downsize is performed. Nevertheless, even the semiconductor detector including a signal processing section has limitations to downsize it. Additionally, such a semiconductor detector needs application of high voltage for measurement; here is a problem in which it is hard to insert the detector into the body and take dose measurements. Furthermore, such a detector is, commonly, of high density and its interaction with radiation is larger as compared with substances in the body and water; here is a problem in which influence of the detector itself is not negligible.

In conditions where actual doses absorbed in the body cannot be identified as noted above, a dose distribution in a therapy plan has margins taking body motion and others into account, which becomes a bottleneck in further improving the precision of radiation irradiation. Moreover, if a normal site that is sensitive to radiation exists near a therapeutic target site, radiation therapy is hard to perform, and identifying doses absorbed in the body is desired.

Therefore, it is desired to place a dosemeter in the body and measure doses inside the body directly during irradiation of radiation, and a smaller and compact fiber type dosemeter with low invasiveness is promising. However, when high-speed electrons generated by irradiation of radiation enter an optical fiber, the electrons generate Cherenkov light; therefore, the generation of Cherenkov light during irradiation of radiation is a problem of an optical fiber type dosemeter.

One of countermeasures against the above-noted problems is a technology described in Patent Literature 1, mentioned above, as the technology in brachytherapy to perform treatment with small radioactive sources being inserted into the body.

Meanwhile, especially, in therapy with X rays and electron beams having high energy and, furthermore, in particle beam therapy, high intensity radioactive rays are irradiated for a short period of time and, hence, a huge amount of Cherenkov light is generated. Therefore, in the case of radiation therapy using an accelerator in this way, a way of noise reduction using an optical filter described in Patent Literature 1 mentioned above does not necessarily produce a sufficient effect, and further reduction of Cherenkov light is desired.

Thus, in order to measure doses inside the body, it is very important that a dosimeter is smaller and less invasive, and, moreover, the influence of Cherenkov light generated inside an optical fiber is reduced, as described previously.

Therefore, a challenge of the present invention is to provide a radiation monitoring device, a radiation therapy apparatus, and a radiation monitoring method enabling it to take real-time measurements of doses inside the body, while reducing influence of Cherenkov light generated inside an optical fiber with a smaller and less invasive device.

Solution to Problem

The present invention includes plural means for solving the above-noted problems and one example of such means is characterized by comprising a scintillator portion which emits light whose intensity depends on a dose of incident radiation, an optical fiber which transmits photons generated in the scintillator portion, a photoelectric converter which converts photons transmitted by the optical fiber to electric signals, a signal counter which counts each of the electric signals after being converted by the photoelectric converter with a certain dead time adjusted relative to time width of an irradiation pulse of radiation, a dose calculation unit which calculates a dose from a signal count value counted by the signal counter, and a display unit which displays a result of measurement calculated by the dose calculation unit.

Advantageous Effects of Invention

According to the present invention, it is enabled to take real-time measurements of doses inside the body, while reducing influence of Cherenkov light generated inside the optical fiber with a smaller and less invasive device.

DESCRIPTION OF EMBODIMENTS

Figure 1:
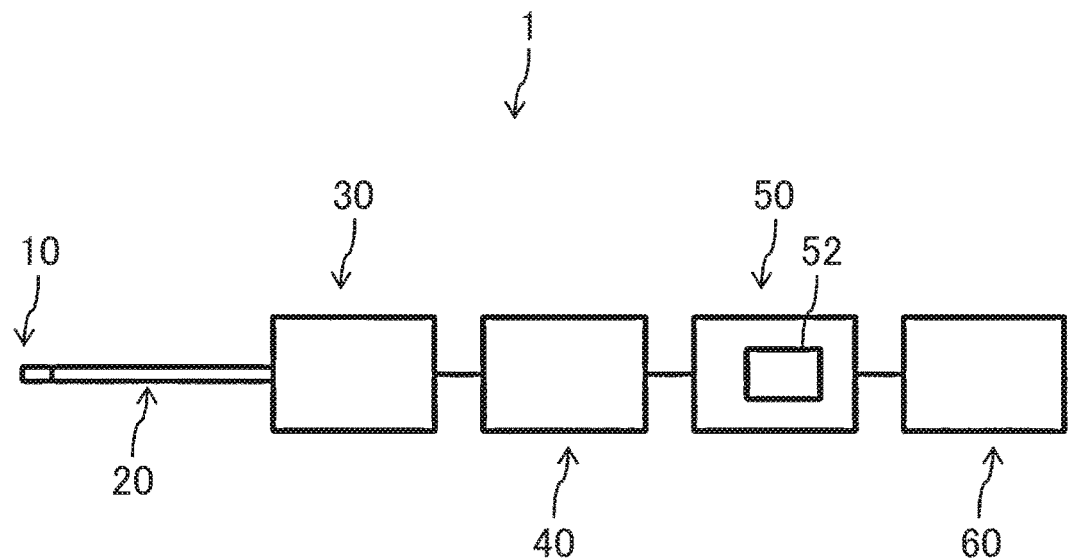
FIG. 1 is a structural diagram of a radiation monitoring device pertaining to a first embodiment.

In the following, embodiments for implementing (hereinafter referred to as "embodiments") a radiation monitoring device, a radiation therapy apparatus, and a radiation monitoring method according to the present invention will be described in detail with reference to the drawing, as appropriate.

First Embodiment

Figure 2:
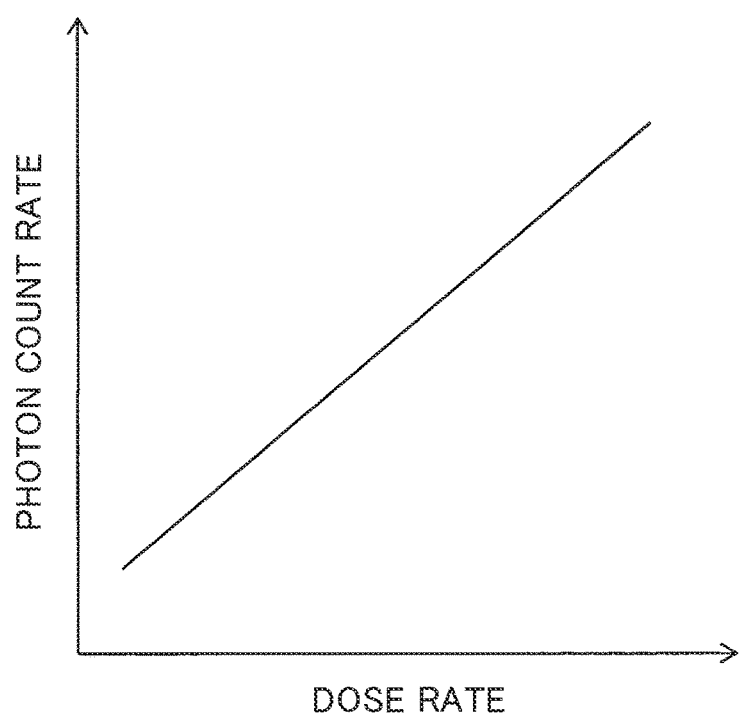
FIG. 2 is a diagram of a relationship between dose rate and photon count rate, pertaining to the first embodiment.
Figure 3:
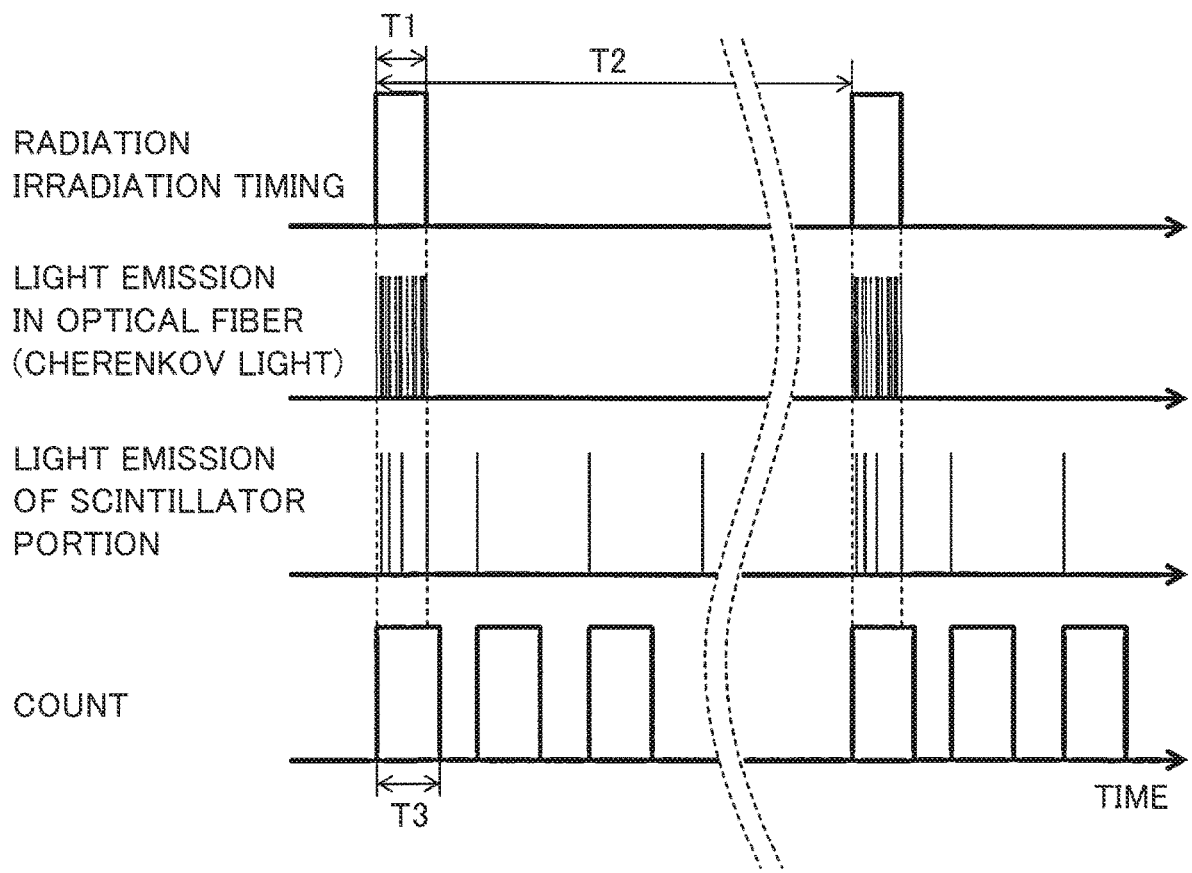
FIG. 3 is a time chart regarding radiation irradiation timing and, inter alia, light emission states of Cherenkov light and a scintillator portion, pertaining to the first embodiment.

A first embodiment of a radiation monitoring device according to the present invention is described with FIGS. 1 through 3. FIG. 1 is a structural diagram of a radiation monitoring device 1 pertaining to the present embodiment. FIG. 2 is a diagram of a relationship between dose rate and photon count rate. FIG. 3 is a time chart regarding radiation irradiation timing and, inter alia, light emission states of Cherenkov light and a scintillator portion.

In FIG. 1, the radiation monitoring device 1 is configured including a scintillator portion 10, an optical fiber 20, a signal counter 40, a photoelectric converter 30, a dose calculation unit 50, and a display unit 60.

The scintillator portion 10 is made of a radiation scintillating material which emits light whose intensity depends on a dose of incident radiation. The radiation scintillating material contains at least one rare earth element species. Specifically, the radiation scintillating material consists of, for example, a material such as transparent Yttrium Aluminum Garnet as a base material and rare earth elements such as ytterbium, neodymium, cerium, and praseodymium contained in the material.

Owing to that the radiation scintillating material contains at least one rare earth element species, as above, it is possible to improve linearity between the dose rate of radiation incident on the scintillator portion 10 and the intensity of light. The radiation monitoring device 1 can take more accurate measurements of a radiation dose rate, even when radiation at a high dose rate is incident thereon.

And now, the scintillator portion 10 is not thus limited and a radiation scintillating material composed of different elements may be used.

The optical fiber 20 is connected with the scintillator portion 10 and transmits photons generated in the scintillator portion 10 to the photoelectric converter 30 which is connected to the other end thereof. A material of which the optical fiber 20 is made may be, for example, quarts, plastics, etc. Although a soft material is better in terms of easiness of handling, it is desired to take radiation resistance into account. Additionally, a fiber cover may be provided for shading or the like, though it is not detailed.

The photoelectric converter 30 is connected to the other end of the optical fiber 20, opposite to one end of the fiber to which the scintillator portion 10 is connected and this converter generates one electric pulse for one photon transmitted thereto. As the photoelectric converter 30, a photomultiplier tube, an avalanche photodiode, etc. may be used. By using the photomultiplier tube among others, photons can be converted to electric pulses with current amplified. Additionally, an amplifier or the like for amplification and waveform shaping of an output signal from the photoelectric converter 30 may be provided, as required, though it is not specified.

The signal counter 40 is connected with the photoelectric converter 30, counts each of electric pulse signals after being converted and amplified by the photoelectric converter with a certain dead time adjusted relative to time width of an irradiation pulse of radiation, and calculates a signal count value. The signal counter 40 in the present embodiment is a non-paralytic type in which, even when a subsequent signal is input within a dead time, the dead time is not extended and counts each of electric signals after being converted by the photoelectric converter 30 with the dead time that is longer than the time width of an irradiation pulse of radiation. Details will be described later.

The dose calculation unit 50 is connected with the signal counter 40, converts a signal count value calculated by the signal counter 40 to a dose of radiation, and outputs a display signal to the display unit 60.

The present inventors found from an experiment that there is a one-to-one correspondence relation between the dose rate of incident radiation and the number of photons emitted per unit time (hereinafter also referred to as a "photon count rate") by the scintillator portion 10, as presented in FIG. 2. On the other hand, it is publicly known that there is a one-to-one correspondence relation between the photon count rate and the count rate of electric pulses. Hence, because it is derived that there is a one-to-one correspondence relation between the dose rate of radiation and the count rate of electric pulses, an obtained count rate of electric pulses can be converted to a dose rate of radiation by using this relation.

Specifically, the dose calculation unit 50 is provided with a storage unit 52 within it to store a data table mapping between count values of electric pulses and doses of radiation and performs calculation processing to convert a count value of electric pulses counted to a dose of radiation. Here, in the dose calculation unit 50, a count value and a dose can be converted into a count rate and a dose rate which are values per unit time of each of them, and a data table for either conversion may be used. Besides, because the above-mentioned correspondence relation between the dose rate of radiation and the count rate of electric pulses differs depending on, inter alia, the size, shape, and material of the scintillator portion 10 that is used and the thickness and length of the optical fiber 20, this correspondence relation should be determined beforehand for each radiation monitoring device 1 and stored as a data table, so that an obtained count rate of electric pulses can be converted to a dose rate of radiation. And now, those that can be obtained with the dose calculation unit 50 are not limited to doses and dose rates of radiation and may be, for example, dose rate change over time among others.

The display unit 60 receives input of a display signal from the dose calculation unit 50 and displays doses and dose rates calculated by the dose calculation unit 50. The display unit 60 can, of course, display other relevant information such as a measurement time and various conditions for measurement.

With FIG. 3, the following gives a description of timing of radiation irradiation, light emission of the scintillator portion 10, and emission of Cherenkov light from the optical fiber 20.

For example, in the case of X-ray therapy apparatus, X rays are irradiated in a pulse shape with several μsec width in a several msec period. Cerenkov light is generated when high-speed electrons move inside the optical fiber 20 and its generation is synchronous with radiation irradiation. On the other hand, the scintillator portion 10 has a characteristic in which light emission is observed even after irradiation by a fluorescence lifetime that depends on its material.

Therefore, if light emission of the scintillator portion 10 can be measured immediately after the irradiation, while not performing the measurement during the radiation, measurement can be made with influence of Cherenkov light being eliminated as much as possible. To do so, an irradiation timing signal has to be captured; nevertheless, there is a need for an additional device depending on radiation equipment and this complicates the device structure and contravenes downsizing.

Therefore, the present embodiment adopts the signal counter 40 in which, inter alia, various time constants of its internal circuits are adjusted so that a dead time T3 for event measurement will be longer than the pulse width T1 of an irradiation pulse of radiation. Thus, this makes a natural reduction in influence of Cherenkov light and implements a simple device configuration without need of an additional device.

A photomultiplier tube for use as the photoelectric converter 30 is commonly high speed and width of an electric pulse signal to which each of photons is converted and which is output is on the order of several nsec. However, electric pulse signals which are output by the photoelectric converter 30 are weak and it is a common practice to amplify them with a preamplifier, an amplifier, or the like and shape their waveform. A dead time occurs in the measurement system when doing so; however, in the present invention, the dead time T3 is adjusted to be longer than the time width T1 of an irradiation pulse of radiation (T3≥T1).

Here, envisioning a commonly used measurement system, the signal counter 40 following the photoelectric converter 30 is made to have a dead time; however, the photoelectric converter 30 and the signal counter 40 may be unified and a section of the photoelectric converter 30 may be made to have a circuit in which the dead time T3 is adjusted to be longer than the width T1 of an irradiation pulse of radiation, furthermore, the dose calculation unit 50 and the display unit 60 may be unified into them and it is satisfactory that the radiation monitoring device 1 as a whole can adjust the dead time to a certain length of time relative to the width of an irradiation pulse of radiation.

By making the dead time T3 longer than the time width T1 of an irradiation pulse of radiation, it is enabled to count only one time of generation of Cherenkov light which is generated many times during an irradiation pulse of radiation and remove other generations. This one-time count can be sufficiently smaller than a count of light emissions by the scintillator portion 10 and, therefore, can be neglected.

Specifically, and because this count that is equal to a count of irradiation pulses with about 1 msec period is about 1 kcps at a maximum, the count of light emissions by the scintillator portion 10 is 100 kcps or more, influence of Cherenkov light will be less than 1% and negligible.

It is desirable that a dead time for the signal counter 40 in the radiation monitoring device 1 according to the present embodiment is fundamentally a non-paralytic type, i.e., even when a subsequent signal is input within a dead time, the dead time is not extended. However, even for a measurement system of a paralytic type in which, when a subsequent signal is input within a dead time, the dead time is extended, such system can be applied preferably, if the time extension is so short that it can be regarded as negligible as against the frequency of light emission of the scintillator portion 10 and a difference between the time width of an irradiation pulse of radiation and the dead time.

A dead time for the signal counter 40 is configurable by preset conditions, and the operator of the radiation monitoring device 1 is allowed to set a dead time based on radiation irradiation conditions (radiation energy, radiation intensity, etc.). Also, an appropriate dead time can be set with reference to conditions retained beforehand after receiving input of radiation irradiation conditions from a control device to control radiation irradiation and a radiation irradiation planning device (omitted from depiction).

The following describes advantageous effects of the present embodiment.

The above-described radiation monitoring device 1 according to the first embodiment of the present invention includes the scintillator portion 10 which emits light whose intensity depends on a dose of incident radiation, the optical fiber 20 which transmits photons generated in the scintillator portion 10, the photoelectric converter 30 which converts photons transmitted by the optical fiber 20 to electric signals, the signal counter 40 which counts each of electric signals after being converted by the photoelectric converter 30 with a certain dead time adjusted relative to time width of an irradiation pulse of radiation, the dose calculation unit 50 which calculates a dose from a signal count value counted by the signal counter 40, and the display unit 60 which displays a result of measurement calculated by the dose calculation unit 50.

By setting the dead time to coincide with timing of generation of Cherenkov light, as noted previously, measurement can be made with reduced influence of Cherenkov light which is noise without measuring radiation irradiation timing actively and precision can be improved significantly. Additionally, according to the present device configuration, it is not needed to add a special measurement device to the optical fiber type dosimeter and a simple measurement system, in other words, reducing measurement equipment cost can be realized. These advantageous effects make it possible to take real-time measurements of doses inside the body during radiation therapy and radiation measurements of high precision for QA/QC (Quality Control) of therapy apparatus, while reducing influence of Cherenkov light with a smaller and less invasive device.

Therefore, use of the above-described device enables dose irradiation at high precision with reduced impacts of body motion, change over time of organs, etc. and also makes it possible to realize enhancement of radiation therapy such as reducing the dose of irradiation in a normal site and expanding a radiation therapy application range.

Besides, the signal counter 40 counts each of electric signals after being converted by the photoelectric converter 30 with the dead time that is longer than the time width of an irradiation pulse of radiation; therefore, the counter counts little of Cherenkov light which is generated in large amounts during radiation irradiation and, after radiation irradiation, counting involved with light emission of the scintillator portion 10 occurring for a longer period as against the width of the irradiation pulse of radiation can be performed at higher precision.

Furthermore, the signal counter 40 is a non-paralytic type in which, even when a subsequent signal is input within a dead time, the dead time is not extended; thereby, it can be avoided that the dead time is extended longer than needed due to Cherenkov light which is generated in large amounts during irradiation and counting signals of light emission of the scintillator portion 10 occurring after radiation irradiation can be performed at higher precision.

Second Embodiment

Figure 4:
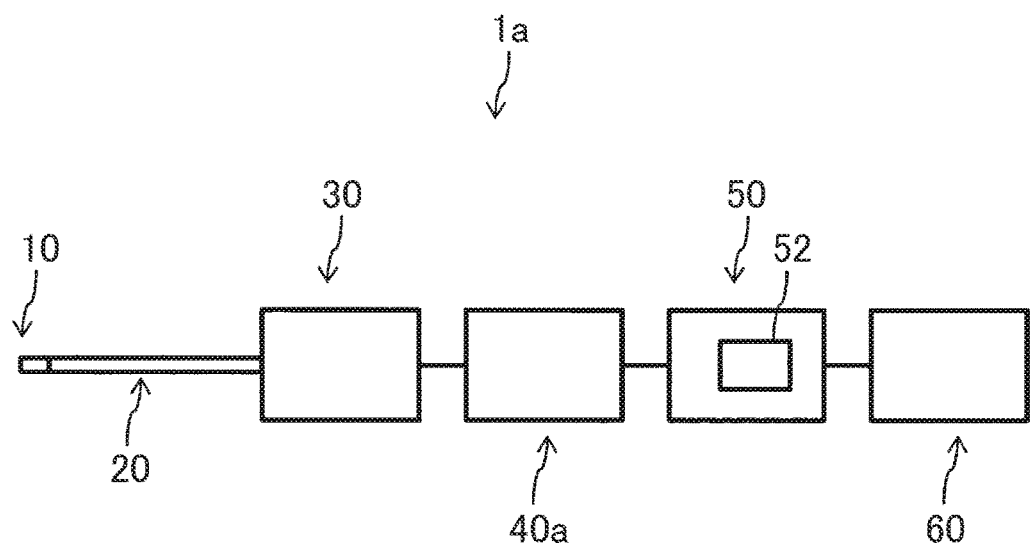
FIG. 4 is a structural diagram of a radiation monitoring device pertaining to a second embodiment.
Figure 5:
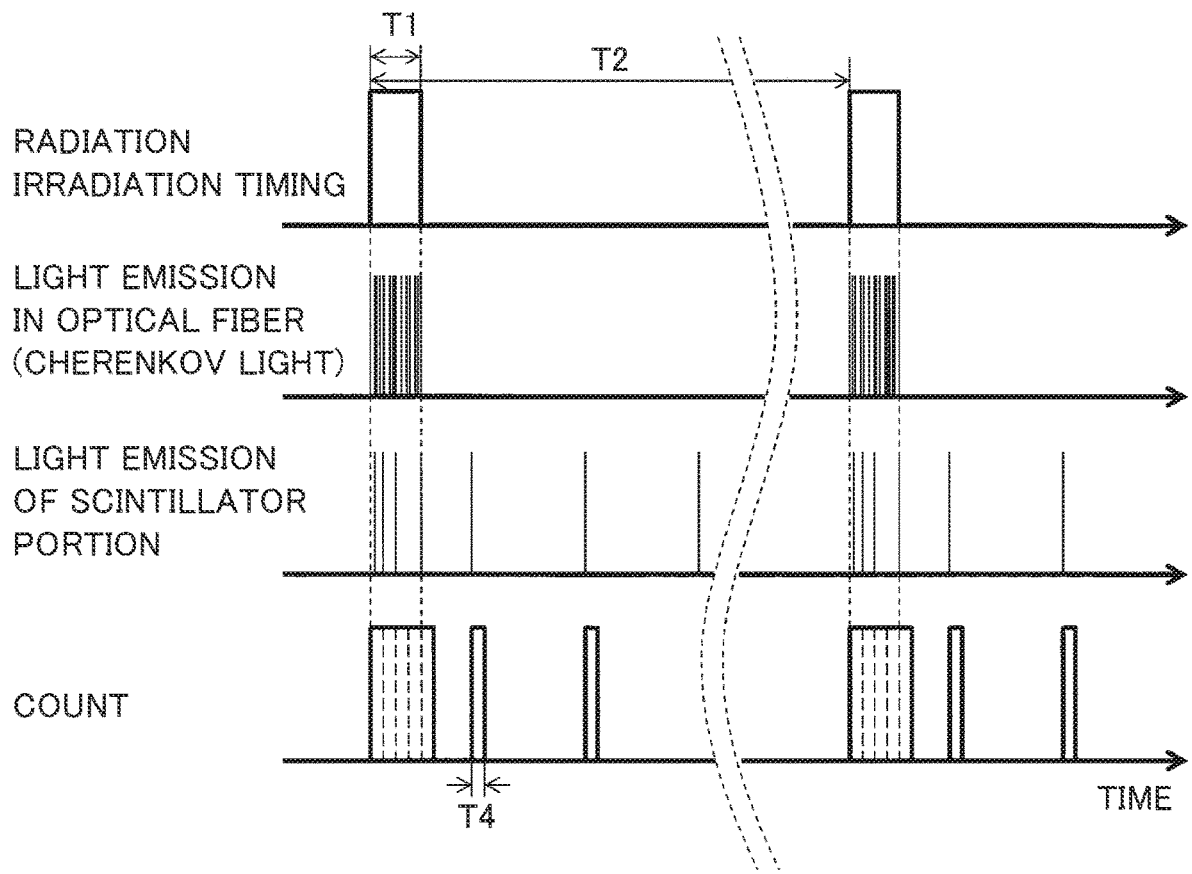
FIG. 5 is a time chart regarding radiation irradiation timing and, inter alia, light emission states of Cherenkov light and the scintillator portion, pertaining to the second embodiment.

A radiation monitoring device according to a second embodiment of the present invention is described with FIGS. 4 and 5. FIG. 4 is a structural diagram of a radiation monitoring device 1a pertaining to the present embodiment. FIG. 5 is a time chart regarding radiation irradiation timing and, inter alia, light emission states of Cherenkov light and a scintillator portion. Components that are identical to those in the first embodiment are marked with identical designators and their description is not repeated. The same applies for succeeding embodiments.

As depicted in FIG. 4, the radiation monitoring device 1a according to the present embodiment is configured including a scintillator portion, an optical fiber 20, a photoelectric converter 30, a signal counter 40a, a dose calculation unit 50, and a display unit 60. Difference from the radiation monitoring device 1 according to the first embodiment lies in that a dead time for the signal counter 40a is shorter than the time width of an irradiation pulse of radiation and it is a paralytic type in which, when a subsequent signal is input within a dead time, the dead time is extended. Therefore, the following describes the signal counter 40a in detail.

As for a dead time that the signal counter 40a in the present embodiment has, the dead time T4 for measurement of one signal is shorter than the time width T1 of an irradiation pulse or radiation (T4≤T1), as depicted in FIG. 5, and, furthermore, it is a paralytic type, i.e., when a subsequent signal is input within a dead time, the dead time is extended. Thereby, the dead time is extended during a period of radiation irradiation, when large amounts of Cherenkov light are generated, and continues over the period, as depicted in FIG. 5.

As with the first Embodiment, a dead time for the signal counter 40a in the present embodiment is configurable by a preset condition and the operator of the radiation monitoring device 1a can set the dead time based on radiation irradiation conditions. Also, an appropriate dead time can be determined with reference to conditions retained beforehand after receiving input of radiation irradiation conditions from the control device to control radiation irradiation and the radiation irradiation planning device.

Other aspects of configuration and operation are substantially the same as those of the radiation monitoring device 1 according the first embodiment described previously.

Also with the radiation monitoring device 1a according to the second embodiment of the present invention, substantially the same advantageous effects are obtained as for the radiation monitoring device 1 according to the first embodiment, which has been described previously.

Besides, the signal counter 40a counts each of electric signals after being converted by the photoelectric converter 30 with the dead time that is shorter than the time width of an irradiation pulse of radiation; thereby, it is possible to reduce possibility of failing to count signals from the scintillator portion 10, occurring because of a long dead time, and measurement sensitivity is improved effectively and precision is further improved.

Furthermore, the signal counter 40a is a paralytic type in which, when a subsequent signal is input within a dead time, the dead time is extended; thereby, a dead state can be maintained during a period of radiation irradiation, since Cherenkov light is generated in large amounts for this period, and counting is deactivated, so that influence of Cherenkov light can be eliminated effectively.

And now, the signal counter 40a in the present embodiment may be a non-paralytic type, not limited to a paralytic type. Even for the non-paralytic type, after a paralytic state is removed, the signal counter 40a is soon paralyzed by Cherenkov light which is generated in large amounts during radiation irradiation and placed in a dead state again and counting can be deactivated, so that influence of Cherenkov light can be eliminated effectively.

Third Embodiment

Figure 6:
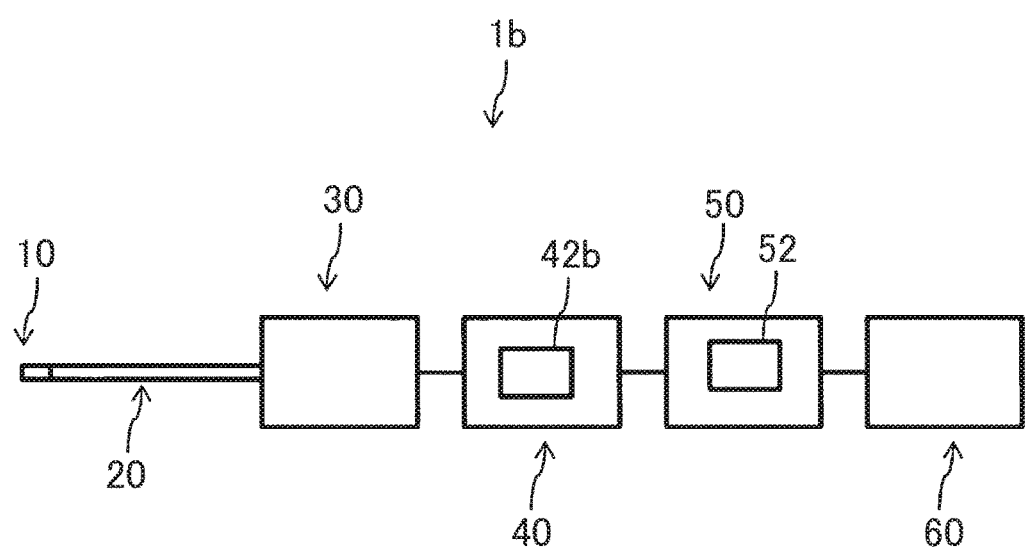
FIG. 6 is a structural diagram of a radiation monitoring device pertaining to a third embodiment.

A radiation monitoring device 1b according to a third embodiment of the present invention is described with FIG. 6. FIG. 6 is a structural diagram of the radiation monitoring device 1b pertaining to the present embodiment.

As depicted in FIG. 6, the radiation monitoring device 1b according to the present embodiment is configured including a scintillator portion 10, an optical fiber 20, a photoelectric converter 30, a signal counter 40b, a dose calculation unit 50, and a display unit 60. Main difference from the radiation monitoring device 1 according to the first embodiment and the radiation monitoring device 1a according to the second embodiment lies in that the signal counter 40b has a compensation device 42b which compensates influence of Cherenkov light. Therefore, the following describes the signal counter 40b in detail.

In the first and second embodiments, influence of Cherenkov light which is generated during radiation irradiation on counting is regarded as limited and negligible; whereas, influence of Cherenkov light on counting is compensated in the present embodiment.

Specifically, when the dead time for the signal counter 40b is longer than the width of an irradiation pulse of radiation, a count attributed to Cherenkov light becomes substantially equal to the number of irradiation pluses of radiation in either case of non-paralytic or paralytic type. The compensation device 42b subtracts, as noise, the number of irradiation pluses of radiation as the count attributed to Cherenkov light from the signal count value that has been counted.

Besides, when the dead time for the signal counter 40b is shorter than the width of an irradiation pulse of radiation and it is a paralytic type, a count attributed to Cherenkov light becomes substantially equal to the number of irradiation pluses of radiation. The compensation device 42b subtracts, as noise, the number of irradiation pluses of radiation as the count attributed to Cherenkov light from the signal count value that has been counted.

Besides, when the dead time for the signal counter 40b is shorter than the width of an irradiation pulse of radiation and it is a non-paralytic type, a count attributed to Cherenkov light correlates with the number of irradiation pulses of radiation. For example, the count attributed to Cherenkov light can be calculated by a ratio of the dead time for the signal counter 40b to the width of an irradiation pulse of radiation (for example, a value obtained by dividing the width of an irradiation pulse of radiation by the dead time becomes equal to the count attributed to Cherenkov light) and the number of irradiation pulses. The compensation device 42b subtracts, as noise, the count attributed to Cherenkov light from the signal count value that has been counted.

The number of irradiation pulses of radiation can be obtained from radiation irradiation conditions (radiation energy, dose rate, irradiation time, etc.) and is configurable by inputting radiation irradiation conditions in advance. Alternatively, radiation pulse timing signals or the like may be acquired from radiation irradiation equipment and counted.

The dose calculation unit 50 in the present embodiment calculates a dose from a compensated signal count value compensated by the compensation device 42b in the signal counter 40b.

Other aspects of configuration and operation are substantially the same as those of the radiation monitoring device 1 according the first embodiment described previously and details thereof are omitted.

Also with the radiation monitoring device 1b according to the third embodiment of the present invention, substantially the same advantageous effects are obtained as for the radiation monitoring device 1 according to the first embodiment and the radiation monitoring device 1a according to the second embodiment, which have been described previously.

Besides, the signal counter 40b has the compensation device 42b which compensates noise in the signal count value that has been counted, based on the number of irradiation pulses of radiation, and the dose calculation unit 50 calculates a dose from a compensated signal count value compensated by the compensation device 42b; thereby, direct influence of Cherenkov light can be eliminated. Therefore, even when the counter counts a smaller number of signals, for instance, when low-dose irradiation is performed or the scintillator portion with low sensitivity is used, noise attributed to Cherenkov light can be reduced more effectively and measurement of higher precision can be performed.

Fourth Embodiment

A radiation monitoring device according to a fourth embodiment of the present invention is described below.

A basic configuration of the radiation monitoring device according to the present embodiment is the same as the configuration of the radiation monitoring device according to any of the first through third embodiments. Difference between these embodiments and the present embodiment only lies in the scintillation lifetime of the scintillator portion 10 and characteristics of the scintillator portion 10 are described in detail.

In the following, consideration is made for the scintillation lifetime of the scintillator portion 10 and emission intensity at measurement timing.

In X-ray therapy, irradiation of X-rays produced by accelerating electrons by an accelerator is performed and, commonly, the irradiation time is several μsec. and the period is several msec. Hence, measurement time is about 1000 times as much as the irradiation time and emission (irradiation) time of the scintillator portion 10 can be considered as zero approximately. Also, we take $\tau$ to stand for the scintillation lifetime of the scintillator portion 10 and T1 and T2 to stand for the pulse length and pulse interval of an irradiation pulse of radiation, respectively.

A first condition of the scintillation lifetime is that light emission of the scintillator portion 10 by pulse irradiation shall attenuate sufficiently until the next radiation pulse irradiation. Specifically, assuming that pulse irradiation occurs n times within the shortest time of treatment and a measurement error is within a %, by a relationship with $n\exp(-T2/\tau)<a$, a conditional expression is as below:

$$\tau < T2/1n(n/a) \tag{1}$$

Here, it is desired that the pulse interval T2 is 10 msec. at longest, the number of times of pulse irradiation is one at minimum, and, as the measurement error, an allowable error of a dose obtained is 3% at maximum. By the expression (1), it is desired that the scintillation lifetime T of the scintillator portion 10 is 2.8 msec. or shorter.

A second condition of the scintillation lifetime is that the amount of luminescence after the pulse length T1 shall be b % or more of the total amount of luminescence. By a relationship with $\exp(-T1/\tau)>b$, this is expresses as:

$$\tau > T1/1n(1/b) \tag{2}$$

Here, the pulse length is 1 μsec. at shortest and the required emission ratio b is at least 10%. By the expression (2), it is desired that the scintillation lifetime T of the scintillator portion 10 is 430 nsec. or longer.

Also with the radiation monitoring device according to the fourth embodiment of the present invention, substantially the same advantageous effects are obtained as for the radiation monitoring device 1 according to the first embodiment and others, which have been described previously.

Besides, by setting the scintillation lifetime T of the scintillator portion 10 to 2.8 msec. or shorter, the measurement error due to afterglow for multiple times of pulse irradiation can be made to fall within 3%. Also, by setting the scintillation lifetime T of the scintillator portion 10 to 430 nsec. or longer, it is enabled to measure 10% or more of emission intensity and an improvement in measurement precision can be achieved with sufficient signal intensity.

Fifth Embodiment

Figure 7:
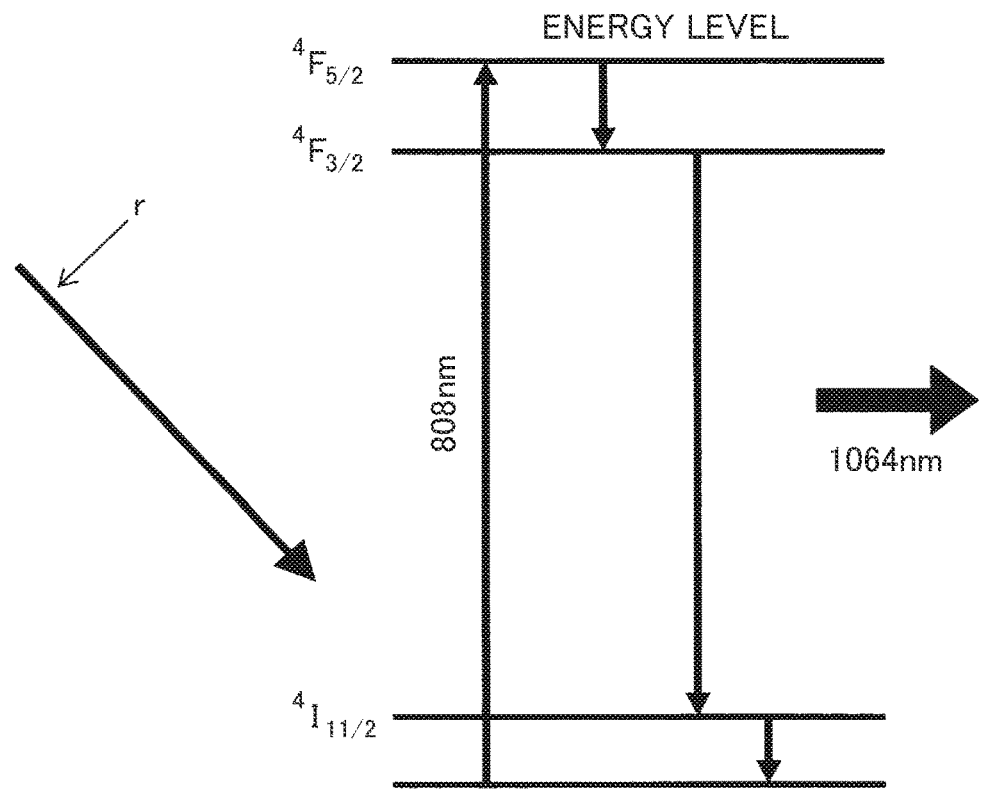
FIG. 7 is a conceptual diagram depicting a process of generation of photons (light) by radiation incident on the scintillator portion made of Nd:YAG crystal, pertaining to a fifth embodiment.

A radiation monitoring device according to a fifth embodiment of the present invention is described with FIG. 7. FIG. 7 is a conceptual diagram depicting a process of generation of photons (light) by radiation incident on the scintillator portion made of Nd:YAG crystal pertaining to the present embodiment.

A basic configuration of the radiation monitoring device according to the present embodiment is the same as the configuration of the radiation monitoring device according to any of the first through fourth embodiments. Difference between these embodiments and the present embodiment only lies in that the scintillator portion 10 is limited to that made of Nd doped YAG (garnet structure crystal consisting of complex oxides of Yttrium and Aluminum ($Y_3AL_5O_{12}$)) and characteristics of the scintillator portion 10 is described in detail.

Nd:YAG which is Nd doped YAG crystal is widely used as a laser material and this crystal absorbs light mainly in a wavelength band between 750 nm and around 800 nm and emits light of a wavelength of 1064±10 nm for a scintillation lifetime of about 230 μsec.

FIG. 7 depicts a principle of light emission of Nd:YAG. As depicted in FIG. 7, when radiation (r) is incident on the Nd:YAG crystal, electrons in the ground state are excited in an absorption band ($^4F_{5/2}$) by interaction between the radiation and the Nd:YAG crystal. Electrons excited in the absorption band make a non-radioactive transition to a laser upper level ($^4F_{3/2}$) and emits photons (1064 nm) when further making a transition from the laser upper level ($^4F_{3/2}$) to a laser lower level ($^4I_{11/2}$) of low excitation energy. Electrons are also excited by interaction with light, not only radiation, but wavelength thereof is mainly 808 nm.

Besides, as described previously, the present inventors have experimentally confirmed that there is a one-to-one correspondence relation between the dose rate of radiation incident on the Nd:YAG scintillator portion 10 and the number of photons emitted per unit time by the scintillator portion 10, as presented in FIG. 2.

Hence, it is possible to transmit photons of 1064 nm emitted by the Nd:YAG scintillator portion 10 to the photoelectric converter 30 through the optical fiber 20, convert each of the photons to an electric pulse signal by the photoelectric converter 30, perform photon counting by the signal counter 40, 40a, 40b, and calculate a dose and a dose rate by the dose calculation unit 50.

Because the scintillation lifetime of the Nd:YAG crystal is 230 μsec., sufficiently longer than the pulse length (several μsec.) of an irradiation pulse of radiation, it is possible to take sufficient count measurements even through measurement after a dead time occurring because of Cherenkov light. Also, the scintillation lifetime of 230 μsec. is sufficiently shorter than the pulse period (several msec.) of an irradiation pulse of radiation, influence attributed to afterglow is small during even a long time of pulse irradiation, and measurements of high precision can be taken.

Thus, also with the radiation monitoring device according to the fifth embodiment of the present invention, substantially the same advantageous effects are obtained as for the radiation monitoring device 1 according to the first embodiment and others, which have been described previously.

Use of the Nd:YAG crystal as the scintillator portion 10 enables it to measure a dose and a dose rate at higher precision, while eliminating Cherenkov light.

Sixth Embodiment

Figure 8:
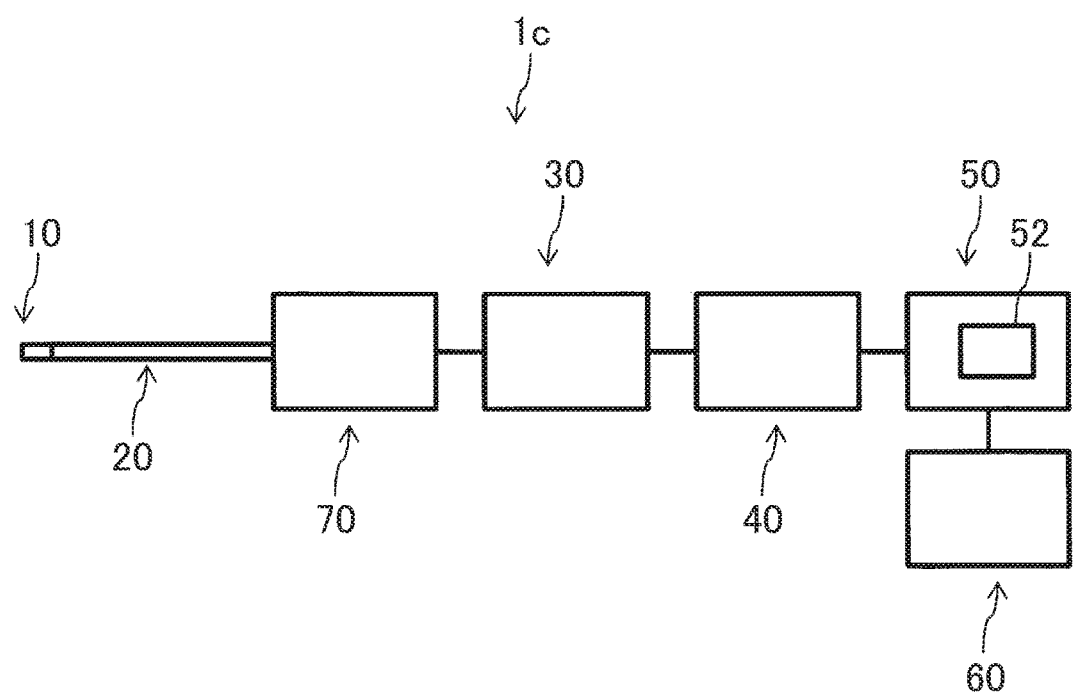
FIG. 8 is a structural diagram of a radiation monitoring device pertaining to a sixth embodiment.

A radiation monitoring device according to a sixth embodiment of the present invention is described with FIG. 8. FIG. 8 is a structural diagram of a radiation monitoring device 1c pertaining to the present embodiment.

As depicted in FIG. 8, the radiation monitoring device 1c according to the present embodiment is comprised including a scintillator portion 10 which is Nd:YAG crystal, an optical fiber 20, a photoelectric converter 30, a signal counter 40, a dose calculation unit 50, and a display unit 60. Difference from the radiation monitoring device according to the fifth embodiment lies in that a wavelength limiting filter (an optical filter) 70 is installed between the optical fiber 20 and the photoelectric converter 30. Therefore, the following describes the wavelength limiting filter 70 in detail.

Commonly, a wavelength distribution of Cherenkov light is such that an ultraviolet region is most intense and intensity decreases by wavelength to the power of three, as the wavelength becomes longer. Hence, intensity of Cherenkov light at an Nd-YAG emission wavelength of 1064 nm is relatively weak and on a level that it does not affect precision; nevertheless, its influence cannot be eliminated completely and, therefore, there is room for improving precision.

Here, if the passing wavelength of the wavelength limiting filter 70 is set to a narrow range around 1064 nm, it is possible to make incident Cherenkov light to be transmitted to the photoelectric converter 30 as small as possible. However, if Cherenkov light of moderate intensity has been incident on the monitoring device of the present invention, uncertainty is entailed in the counting and deterioration in compensation precision is concerned.

In a case where the monitoring device is equipped with the compensation device 42a, for example, as in the third embodiment, when a dead time has been set longer than the time width of an irradiation pulse of radiation, it will happen that no Cherenkov light is measured during the period of an irradiation pulse of radiation, resulting in that the count attributed to Cherenkov light becomes smaller than the number of irradiation pulses of radiation; therefore, there is room for further improving compensation precision. Also, in this case, timing of incidence of Cherenkov light, i.e., time at which a dead time starts varies. In the worst case, incidence of Cherenkov light occurs immediately before the end of an irradiation pulse of radiation, resulting in a dead time extension that is longer than needed until after the end of an irradiation pulse of radiation and there is a possibility of failing to count signals from the scintillator portion 10; likewise, there is room for improving compensation precision.

Also, in the case of a paralytic type in which a dead time is set shorter than the time width of an irradiation pulse of radiation, incidence of Cherenkov light occurs sparsely, resulting in loss of dead time continuity, and a count attributed to Cherenkov light does not correlate with the pulse width and the number of irradiation pulses of radiation; it is concerned that compensation becomes insufficiently.

Although a commonly used wavelength limiting filter having a narrow passing wavelength band is preferred, the filter allowing passage of emission wavelengths at and around the Nd:YAG emission wavelength, the limiting filter 70 according to the present embodiment allows passage of the Nd:YAG emission wavelength and also positively allows passage of a short wavelength region of wavelengths shorter than 1064 nm. Thereby, it is possible to ensure incidence of Cherenkov light whose intensity (the number of photons) is sufficient and, consequently, this enables appropriate dead time setting and makes improvement in the precision of compensation of Cherenkov light and the measurement precision.

Also with the radiation monitoring device 1c according to the sixth embodiment of the present invention, substantially the same advantageous effects are obtained as for the radiation monitoring device according to the fifth embodiment, which has been described previously.

Besides, the wavelength limiting filter 70 is further installed between the optical fiber 20 and the photoelectric converter 30 and the wavelength limiting filter 70 allows passage of the YAG crystal emission wavelength of 1064 nm and also allows passage of Cherenkov light whose wavelength is shorter than 1064 nm, thereby enabling it to ensure adequate dead times when radiation irradiation is performed. Thus, it is possible to reduce influence of Cherenkov light and measurements of higher precision with further reduced noise can be taken.

Seventh Embodiment

Figure 9:
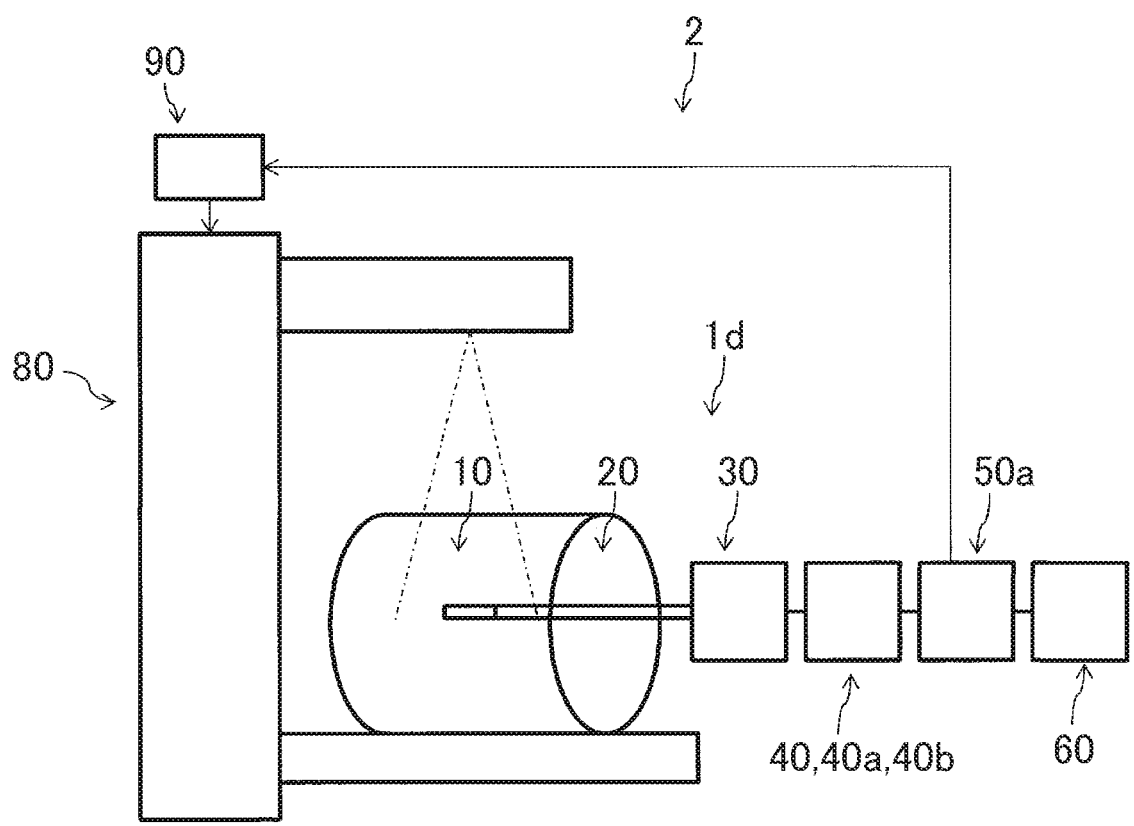
FIG. 9 is a structural diagram of a radiation monitoring device and a radiation therapy apparatus pertaining to a seventh embodiment.

A radiation therapy apparatus according to a seventh embodiment of the present invention is described with FIG. 9. FIG. 9 is a structural diagram of a radiation monitoring device 1d and a radiation therapy apparatus 2 using such device pertaining to the present embodiment.

Ad depicted in FIG. 9, the radiation therapy apparatus 2 according to the present embodiment is comprised of a radiation irradiation equipment which generates and irradiates radiation, a radiation monitoring device 1d having the same configuration as the radiation monitoring devices 1, 1a, 1b, 1c, etc. described in any embodiment of the first through sixth embodiments, a radiation control device 90 which controls the radiation irradiation equipment 80 using doses calculated by the radiation monitoring device 1d.

The radiation monitoring device 1d is configured including a scintillator portion 10, an optical fiber 20, a photoelectric converter 30, a signal counter 40, 40a, 40b, a dose calculation unit 50a, and a display unit 60. Difference from the radiation monitoring devices according the first through sixth embodiments lies in that the dose calculation unit 50a outputs information such as calculated doses to the radiation control device 90 as signals.

In the radiation therapy apparatus 2, the scintillator portion 10 is installed in the vicinity of a measurement target site in the body or within a phantom and online dose measurement is performed as with the first through sixth embodiments during radiation irradiation by the radiation irradiation equipment 80. The radiation control device 90 acquires measured doses from the dose calculation unit 50a, monitors doses in the target site in real time during irradiation, and performs a feedback control such as changing a radiation irradiation condition, as required, thus implementing optical irradiation (radiation therapy).

According to the radiation therapy apparatus 2 according to the seventh embodiment of the present invention, it is enabled by the radiation monitoring device 1d to reduce influence of Cherenkov light and, then, take measurements of doses in the vicinity of the site of interest in the body or the like at high precision and in real time and, therefore, it is further enabled to perform a feedback control of irradiation conditions from measured doses in real time, and highly precise radiation therapy can be realized.

Eighth Embodiment

Figure 10:
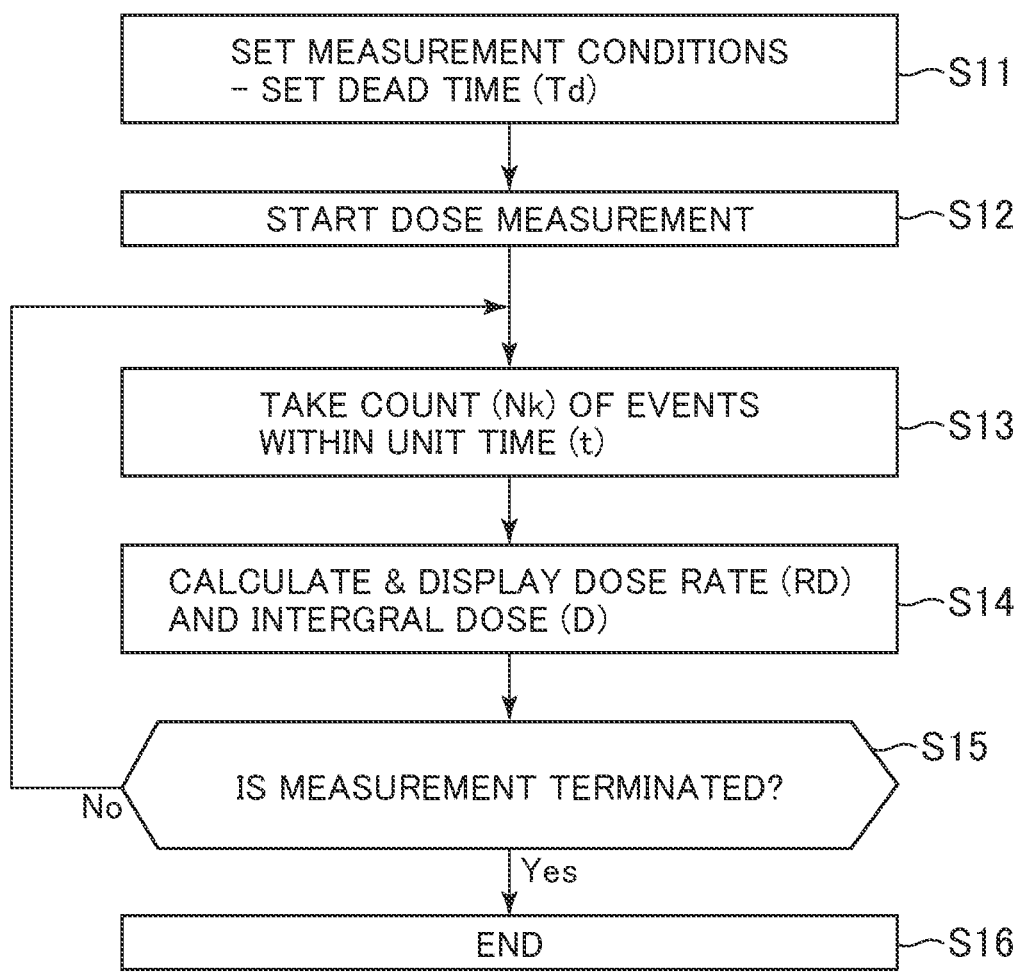
FIG. 10 is a radiation measurement control flow diagram for a radiation monitoring device, pertaining to an eighth embodiment.

A radiation monitoring method according to an eighth embodiment of the present invention is described with FIG. 10. FIG. 10 is a radiation measurement control flow diagram pertaining to the present embodiment.

The configuration of a radiation monitoring device pertaining to the present embodiment is the same as the radiation monitoring devices 1, 1a, 1c, 1d, etc. described in the first, second, and fourth through seventh embodiments and description thereof is omitted.

The radiation monitoring method pertaining to the present embodiment is described with the flowchart in FIG. 10. This processing flow is a control processing flow that is mainly performed by the signal counter 40, 40a and the dose calculation unit 50, 50a.

Step S11

Measurement conditions (irradiation conditions, dead time (Td), etc.) are input by operator action. A major purpose of the present processing is to set a dead time (Td) and the operator is allowed to input a dead time (Td) directly. Also, after acquiring irradiation conditions (radiation energy, radiation intensity, etc.) from the radiation control device 90 and the radiation irradiation planning device (omitted from depiction), the signal counter 40 and the dose calculation unit 50 among others can set an appropriate dead time (Td), referring to the conditions retained beforehand. Besides, this step can be skipped. In that case, a preset dead time (Td) is used.

Step S12

When radiation irradiation is started by operator action, dose measurement starts.

Step S13

Photon counting with the preset dead time (Td) is performed through, inter alia, the scintillator portion 10, optical fiber 20, photoelectric converter 30, and signal counter 40 and a count ($N_k$) within a predetermined unit time (t) is measured. Here, k denotes a count execution number within the unit time. This step S13 corresponds to a series of a light emission step, a transmission step, a photoelectric conversion step, and a signal counting step.

Step S14

The dose calculation unit 50 calculates a dose rate (RD) and a dose (D) from the count $N_k$ counted by the signal counter 40 at step S13 using a conversion table retained beforehand (conversion formulae, equations (3) and (4) below) among others and displays results on the display unit 60.

$$RD = F1(N_k, Td, t) \quad (3)$$

$$D = F2(\Sigma N_k, Td) \quad (4)$$

These conversion formulae, equations (3) and (4) are relational expressions of linearity presented in FIG. 2 and, as a function of dead time Td, a relationship between photon count rate and dose rate or a relationship between photon count and dose should expediently be obtained in advance. This step S14 corresponds to a dose calculation step.

Step S15

It is determined whether a preset measurement termination condition (e.g., irradiation time among others) is fulfilled. If it is determined that the measurement termination condition is not fulfilled, the processing transits to step S13 and the measurement continues. Otherwise, if it is determined that the measurement termination condition is fulfilled, the processing proceeds to the next step S16.

Step S16

Measurement end or the like is displayed on the display unit 60 and the measurement terminates.

According to the radiation monitoring method according to the eighth embodiment of the present invention, it is possible to realize highly precise measurement of doses or dose rates with reduced influence of Cherenkov light. Additionally, because there is no need for special measurement means other than dose measurement means, device simplification and cost reduction can be realized.

Ninth Embodiment

Figure 11:
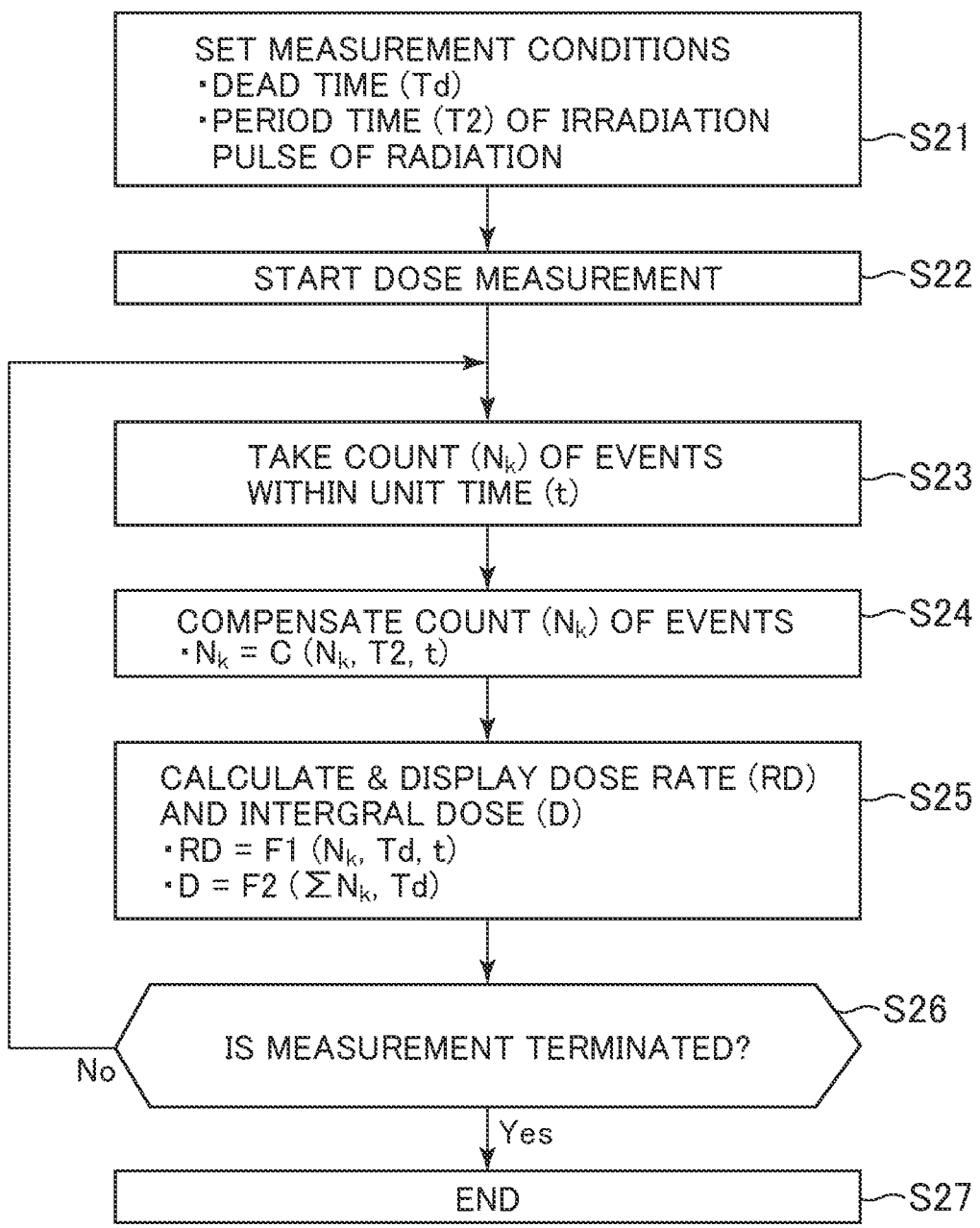
FIG. 11 is a radiation measurement control flow diagram for a radiation monitoring device, pertaining to a ninth embodiment.

A radiation monitoring method according to a ninth embodiment of the present invention is described with FIG. 11. FIG. 11 is a radiation measurement control flow diagram pertaining to the present embodiment.

The configuration of a radiation monitoring device pertaining to the present embodiment is the same as, inter alia, the radiation monitoring device 1b described in, inter alia, the third embodiment and description thereof is omitted.

The radiation monitoring method pertaining to the present embodiment is described with the flowchart in FIG. 11. This processing flow is a control processing flow that is mainly performed by the signal counter 40b and the dose calculation unit 50.

Step S21

Measurement conditions (irradiation conditions, dead time (Td), a period time (T2) of an irradiation pulse of radiation, etc.) are input by operator action. A major purpose of the present processing is to set a dead time (Td) and a period time (T2) of an irradiation pulse of radiation and a dead time (Td) and a period time (T2) of an irradiation pulse of radiation can be input directly. Also, after acquiring irradiation conditions (radiation energy, radiation intensity, etc.) from the radiation control device 90 and the radiation irradiation planning device (omitted from depiction), inter alia, the dose calculation unit 50 can set an appropriate dead time (Td) and an appropriate period time (T2) of an irradiation pulse of radiation, referring to the conditions retained beforehand. Besides, this step can be skipped. In that case, a preset dead time (Td) and a preset period time (T2) of an irradiation pulse of radiation are used.

Step S22

When radiation irradiation is started by operator action, dose measurement starts.

Step S23

Photon counting with the preset dead time (Td) is performed through, inter alia, the scintillator portion 10, optical fiber 20, photoelectric converter 30, and signal counter 40b and a count (Nk) within a predetermined unit time (t) is measured. Here, k denotes a count execution number within the unit time. This step S23 corresponds to a part of a series of a light emission step, a transmission step, a photoelectric conversion step, and a signal counting step.

Step S24

The dose calculation unit 50 compensates $N_k$ counted by the signal counter 40 to exclude influence of Cherenkov light using a compensation table retained beforehand (a compensation formula, equation (5) below) among others.

$$N_k = C(N_k, T2, t) \quad (5)$$

This compensation formula, equation (5) is transformed to equation (6), since it is expedient to subtract the number of irradiation pulses of radiation in a case where the dead time for the signal counter 40b that is simplest is longer than the width of an irradiation pulse of radiation or in the case of a paralytic type where the dead time is shorter than the width of an irradiation pulse of radiation.

$$N_k = N_k - (t/T2) \quad (6)$$

And now, such a compensation formula is not limited to equation (6) and a compensation formula as a function of dead time Td and radiation energy and intensity may be obtained in advance.

This step S24 corresponds to a compensation step which is a part of the signal counting step.

The dose calculation unit 50 calculates a dose rate (RD) and a dose (D) from the event count $N_k$ after being compensated at step S24 using a conversion table retained beforehand (the foregoing equations (3) and (4)) among others. This step S25 corresponds to the dose calculation step.

Step S26

It is determined whether a preset measurement termination condition (e.g., irradiation time among others) is fulfilled. If it is determined that the measurement termination condition is not fulfilled, the processing transits to step S23 and the measurement continues. Otherwise, if it is determined that the measurement termination condition is fulfilled, the processing proceeds to the next step S27.

Step S27

Measurement end or the like is displayed on the display unit 60 and the measurement terminates.

Also with the radiation monitoring method according to the ninth embodiment of the present invention, substantially the same advantageous effects are obtained as for the radiation monitoring method according to the eighth embodiment, which has been described previously, and substantially the same advantageous effects are obtained as for the radiation monitoring device according to the third embodiment, which has been described previously. Besides, because a count $N_k$ is obtained with influence of Cherenkov light being eliminated, a dose rate (RD) or a dose (D) can uniquely be calculated from $N_k$. That is, condition entry of Td in the equations (3) and (4) among others becomes unnecessary and it becomes easy to determine a dose rate (RD) or a dose (D) and, besides, it becomes simple to determine and retain the conditional expression.

Others

And now, the present invention is not limited to the embodiments described hereinbefore and various modifications are included therein. For example, the foregoing embodiments are those described in detail to explain the present invention clearly and the invention is not necessarily limited to those including all components described. A subset of the components of an embodiment can be replaced by components of another embodiment. To the components of an embodiment, components of another embodiment can be added. For a subset of the components of each embodiment, other components can be added to the subset or the subset can be removed or replaced by other components.

LIST OF REFERENCE SIGNS 1, 1a, 1b, 1c, 1d: radiation monitoring device
2: radiation therapy apparatus
10: scintillator portion
20: optical fiber
30: photoelectric converter
40, 40a, 40b: signal counter
42b: compensation device
50, 50a: dose calculation unit
52: storage unit
60: display unit
70: wavelength limiting filter (optical filter)
80: radiation irradiation equipment
90: radiation control device

The invention claimed is:

1. A radiation monitoring device characterized by comprising:
   a scintillator portion which emits light whose intensity depends on a dose of incident radiation;
   an optical fiber which transmits photons generated in the scintillator portion;
   a photoelectric converter which converts photons transmitted by the optical fiber to electric signals;
   a signal counter which counts each of the electric signals after being converted by the photoelectric converter with a certain dead time adjusted relative to time width of an irradiation pulse of radiation,
   a dose calculation unit which calculates a dose from a signal count value counted by the signal counter; and
   a display unit which displays a result of measurement calculated by the dose calculation unit.

2. The radiation monitoring device according to claim 1 characterized in that
   the signal counter counts each of the electric signals after being converted by the photoelectric converter with a dead time that is longer than the time width of an irradiation pulse of radiation.

3. The radiation monitoring device according to claim 2 characterized in that
   the signal counter comprises a compensation device which compensates a counted signal count value to exclude noise, based on the number of irradiation pulses of radiation, and
   the dose calculation unit calculates a dose from a compensated signal count value compensated by the compensation device.

4. The radiation monitoring device according to claim 2 characterized in that
   the signal counter is a non-paralytic type in which, even when a subsequent signal is input within a dead time, the dead time is not extended.

5. The radiation monitoring device according to claim 1 characterized in that
   the signal counter counts each of the electric signals after being converted by the photoelectric converter with a dead time that is shorter than the time width of an irradiation pulse of radiation.

6. The radiation monitoring device according to claim 5 characterized in that
   the signal counter comprises a compensation device which compensates a counted signal count value to exclude noise, based on the number of irradiation pulses of radiation, and
   the dose calculation unit calculates a dose from a compensated signal count value compensated by the compensation device.

7. The radiation monitoring device according to claim 5 characterized in that
   the signal counter is a paralytic type in which, when a subsequent signal is input within a dead time, the dead time is extended.

8. The radiation monitoring device according to claim 1 characterized in that
   The scintillator portion has a scintillation lifetime ranging between 730 nsec. and 2.8 msec., inclusive.

9. The radiation monitoring device according to claim 1 characterized in that
   The scintillator portion is made of Nd doped YAG crystal.

10. The radiation monitoring device according to claim 9 characterized in that
    an optical filter is further installed between the optical fiber and the photoelectric converter, and
    the optical fiber allows passage of an emission wavelength of 1064 nm of the YAG crystal and, also, passage of Cherenkov light with a wavelength shorter than 1064 nm.

11. A radiation therapy apparatus characterized by comprising:
    a radiation irradiation equipment which generates and irradiates radiation;
    a radiation monitoring device described in claim 1; and
    a radiation control device which controls the radiation irradiation equipment using doses calculated by the radiation monitoring device.

12. A radiation monitoring method characterized by comprising:
    a light emission step of emitting light whose intensity depends on a dose of incident radiation;
    a transmission step of transmitting photons generated in the light emission step by an optical fiber;
    a photoelectric conversion step of converting the photons transmitted in the transmission step to electric signals;
    a signal counting step of counting each of the electric signals after being converted in the photoelectric conversion step with a certain dead time adjusted relative to time width of an irradiation pulse of radiation; and
    a dose calculation step of calculating a dose from a signal count value counted in the signal counting step.

13. The radiation monitoring method according to claim 12 characterized in that
the signal counting step comprises a compensation step of compensating a counted signal count value to exclude noise, based on the number of irradiation pulses of radiation, and
the dose calculation step calculates a dose from a compensated signal count value compensated in the compensation step.

* * * * *